United States Patent [19]

Poli

[11] Patent Number: 5,401,470

[45] Date of Patent: Mar. 28, 1995

[54] COMBUSTIBLE GAS SENSOR

[75] Inventor: Albert A. Poli, Pittsburgh, Pa.

[73] Assignee: Mine Safety Appliances Company, Pittsburgh, Pa.

[21] Appl. No.: 873,387

[22] Filed: Apr. 24, 1992

[51] Int. Cl.$^6$ ............................................. G01N 27/16
[52] U.S. Cl. ........................................ 422/96; 422/94; 422/97; 422/98; 436/152
[58] Field of Search ................ 422/88, 94, 97, 98, 422/96; 436/152

[56] References Cited

U.S. PATENT DOCUMENTS

| | | | |
|---|---|---|---|
| 3,954,739 | 5/1976 | Wilkinson | 422/61 X |
| 3,960,495 | 6/1976 | Tantram | 422/97 |
| 4,045,177 | 8/1977 | McNally | 422/96 X |
| 4,072,467 | 2/1978 | Jones | 422/97 X |
| 4,111,658 | 9/1978 | Firth et al. | 422/98 |
| 4,123,225 | 10/1978 | Jones et al. | 422/98 |
| 4,303,612 | 12/1981 | Sonley | 422/94 |
| 4,313,907 | 2/1982 | McNally | 422/96 X |
| 4,332,772 | 6/1982 | McNally | 422/97 |
| 4,355,056 | 10/1982 | Dalla Betta et al. | 422/94 |
| 4,457,954 | 7/1984 | Dabill et al. | 427/125 |
| 4,464,339 | 8/1984 | Wilkinson-Tough | 422/97 |
| 4,533,520 | 8/1985 | Bossart et al. | 422/98 |
| 4,804,632 | 2/1989 | Schuck et al. | 422/97 X |
| 4,806,314 | 2/1989 | Fertig et al. | 422/98 |
| 4,885,929 | 12/1989 | Kasahara et al. | 422/98 |

*Primary Examiner*—Jill A. Johnston
*Assistant Examiner*—Harold Y. Pyon
*Attorney, Agent, or Firm*—James G. Uber

[57] ABSTRACT

A matched catalytically inactive compensator for use in a combustible gas sensor is made from a catalytically active detector. The catalytically active detector is exposed to a gas phase catalytic inhibitor such as hexamethyldisiloxane to completely destroy its catalytic ability thereby forming a compensator which has very similar chemical and physical properties to the untreated detectors.

5 Claims, No Drawings

COMBUSTIBLE GAS SENSOR

FIELD OF THE INVENTION

The present invention relates to a catalytically inactive compensator used with a detector in a combustible gas sensor and to the process for producing the catalytically inactive compensator.

BACKGROUND OF THE INVENTION

It is known to use electrically heatable filaments typically in a helical coil configuration for the detection of combustible gases in air. These filaments are usually embedded within or completely surrounded by an oxide or other refractory material such as alumina or silica so as to form a bead or pellet. Typically a pair of such filament pellets is arranged in a Wheatstone bridge circuit to form a combustible gas sensor. These filament pellets constitute the detecting and compensating pelements respectively.

The detecting pelement is usually formed by the addition of a catalytically active material such as palladium or platinum to the refractory material from which the pellet is made. Alternatively, the filament itself can be made from the catalytically active material. Similarly, the compensating pelement can be usually made by adding a suitable metallic oxide such as chromium oxide or some other catalyst poison or catalytic inhibitor to the material from which the pellet is formed. Such a combustible gas sensor is described in U.S. Pat. No. 3,092,799.

Many different methods have been proposed for making a catalytically inactive compensator for a combustible gas sensor. In U.S. Pat. No. 4,355,056, the compensator can be formed by coating the pelement with metals to form an inactive adherent oxide layer upon oxidation. In U.S. Pat. Nos. 4,123,225 and 4,072,467, the compensator consists of a homogeneous mixture of a non-catalytic carrier material such as alumina and a catalyst poison such as potassium hydroxide to suppress the oxidation of combustible gases. In U.S. Pat. Nos. 4,315,956 and 4,332,772, the compensator is covered with an aqueous solution of cobaltous nitrate and then heated to form a cobalt oxide coating in an attempt to render the compensator catalytically inactive. U.S. Pat. No. 4,313,907 discloses a compensator which is formed by applying a liquid coating of either sodium metasilicate or lead borate in an attempt to render it catalytically inactive. In U.S. Pat. No. 4,045,177 the compensator is coated with an oxide selected from the group consisting of vanadium, columbium, tantalum, chromium, molybdenum, tungsten or uranium to increase the emissivity of the compensator.

One major disadvantage with these compensating elements is that they are physically and chemically different from the detecting element with which they are paired. As a result, they cannot exactly compensate for the changes in temperature, humidity and pressure in the operating environment of the sensor when placed in the Wheatstone bridge circuit. It would be desirable, therefore, to have a catalytically inactive compensator which was practically identical in composition and physical structure to its corresponding detector so that these inherent differences are minimized.

SUMMARY OF THE INVENTION

Generally, the present invention relates to a matched catalytically inactive compensator created from a detector which has been rendered catalytically inactive by exposure to a gas phase catalytic inhibitor such as a silicone-based compound, a phosphorous-based compound or hydrogen sulfide. Preferably the detector comprises a wire coil made from a catalytically active material such as palladium or platinum. The coil is embedded within and surrounded by a refractory material to form a pelement. Alternatively, the catalytically active material can be contained within or coated on the refractory material of the pelement. The compensator is formed by exposing the detector to a gas phase catalyst poison, preferably hexamethyldisiloxane or decamethylcyclpentasiloxane, to render it catalytically inactive and then heating the detector to permanently set the catalytic inactivity and to remove any residual catalyst poison.

The present invention also relates to the method of converting a detector into a compensator by exposing it to a gas phase catalytic inhibitor, preferably having a high vapor pressure, to render the detector catalytically inactive and thus suitable for use as a compensator in a combustible gas sensor. This method of forming compensators from actual detectors enables the detectors to more easily be matched with the compensators since their chemical and physical properties are almost identical.

DESCRIPTION OF THE PREFERRED EMBODIMENT

The compensator of the present invention comprises a detector pelement which has been catalytically deactivated by exposure to a gas phase catalytic poison such as a silicone-based compound or a phosphorous-based compound such as dimethylmethylphosphonate. Preferably, the detector pelement comprises a wire coil made of a catalytically active material such as platinum or palladium, and a ceramic bead made of a refractory material such as alumina or silica which serves as a supporting framework and completely surrounds the wire coil. The ends of the wire coil project from the ceramic bead of refractory material and can be electrically connected with a compensator pelement in a measuring circuit, typically a Wheatstone bridge circuit. The compensator of the present invention is formed by infusing a detector pelement with a silicone-based compound preferably of a high vapor pressure such as hexamethyldisiloxane to make the detector incapable of catalyzing a combustible material and thereby forming a compensator. Any silicone-based compound the vapor of which can diffuse into the pelement can serve as the catalytic poison.

The detector is an active pelement that catalytically burns combustible gases present in the sensor. The compensator, on the other hand, does not react to the presence of combustible gases but does change proportionally to the detector when the operating environment of the sensor changes with respect to temperature, humidity and pressure. The compensator is wired electrically in the Wheatstone bridge circuit so that its changes are reflected opposite to those of the detector, thereby providing for the stabile operation of the sensor when changes take place in the operating environment.

The compensator of the present invention provides several advantages. Initially it should be noted that only one type of pelement needs to be manufactured, namely detectors. Moreover, since the compensators are made from the detectors, the physical and chemical similarity of the pelements is practically identical thereby simplifying the task of matching the detectors and compensators used in a combustible sensor. Other advantages are also expected from the compensator of the present invention such as a longer useful life and a more quiet, drift-free operation thereby permitting the use of higher gain electronics with the sensor.

Preferably the compensator of the present invention is created by starting with a detector made from many known processes including the one as described above. Initially, the detector is heated until the pelement turns a dull red color, typically 600° C. This heating cleans the detector pelement by removing water and other impurities. Next, the detector is exposed to a gas phase catalytic inhibitor such as a silicone-based compound. Preferably this is done by placing the detector above a liquid bath of hexamethyldisiloxane for thirty minutes. Due to the high vapor pressure of hexamethyldisiloxane, this can be done at room temperature and ambient pressure. Finally, the pelement is heated again to a dull red to permanently fix the catalytic inactivity and to eliminate any residual catalytic inhibitor which could poison the detector with which this compensator will be matched when it is placed in a sensor. The initial heating to clean the detector is not necessary but it greatly improves the manufacturing yield.

While a presently preferred embodiment of practicing the invention has been shown and described with particularity, the invention may otherwise be embodied within the scope of the following claims.

What is claimed is:

1. In a sensor for detecting a combustible gas comprising a catalytically active detector and a catalytically inactive compensator, the improvement comprising making the sensor from a plurality of chemically and physically similar catalytically active elements one of said elements being the catalytically active detector and creating the catalytically inactive compensator by taking another of the chemically and physically similar catalytically active elements and rendering it catalytically inactive by exposure to a gas-phase catalytic poison.

2. The sensor as described in claim 1 wherein the gas-phase catalytic poison used to transform one of the catalytically active elements into the catalytically inactive compensator is a silicone-based compound.

3. The sensor as described in claim 2 wherein the silicone-based compound has a vapor pressure sufficient to enable the compound to diffuse into one of the catalytically active elements and render it catalytically inactive thereby forming the catalytically inactive compensator.

4. The sensor as described in claim 3 wherein the silicone-based compound is hexamethyldisiloxane or decamethylcyclpentasiloxane.

5. The sensor as described in claim 1 wherein the gas-phase catalytic poison used to transform one of the catalytically active elements into the catalytically inactive compensator is hydrogen sulfide or a phosphorous-based compound.

* * * * *